(12) United States Patent
Chen

(10) Patent No.: US 11,723,525 B2
(45) Date of Patent: Aug. 15, 2023

(54) DISPOSABLE INTEGRATED ENDOSCOPE

(71) Applicant: HJY Forward Medical Investment Co., Ltd., Ebene (MU)

(72) Inventor: John Jiannyuh Chen, Seattle, WA (US)

(73) Assignee: HJY Forward Medical Investment Co., Ltd.

(*) Notice: Subject to any disclaimer, the term of this patent is extended or adjusted under 35 U.S.C. 154(b) by 294 days.

(21) Appl. No.: 17/116,663

(22) Filed: Dec. 9, 2020

(65) Prior Publication Data
US 2022/0095904 A1 Mar. 31, 2022

(30) Foreign Application Priority Data
Sep. 30, 2020 (TW) ................................. 109134233

(51) Int. Cl.
*A61B 1/05* (2006.01)
*A61B 1/00* (2006.01)
*A61B 1/06* (2006.01)
*A61B 1/12* (2006.01)

(52) U.S. Cl.
CPC ............ *A61B 1/05* (2013.01); *A61B 1/00009* (2013.01); *A61B 1/00103* (2013.01); *A61B 1/00124* (2013.01); *A61B 1/0684* (2013.01); *A61B 1/128* (2013.01); *A61B 2562/166* (2013.01); *A61B 2562/227* (2013.01)

(58) Field of Classification Search
CPC ....... A61B 1/00124; A61B 1/05; A61B 1/051; A61B 1/053; A61B 1/0676; A61B 1/128
See application file for complete search history.

(56) References Cited

U.S. PATENT DOCUMENTS

| | | | |
|---|---|---|---|
| 2008/0151046 A1* | 6/2008 | Scott | A61B 1/12 348/82 |
| 2008/0158349 A1* | 7/2008 | Miller | H04N 5/2256 348/82 |
| 2008/0200758 A1* | 8/2008 | Orbay | A61B 1/313 600/170 |
| 2011/0306834 A1* | 12/2011 | Schrader | G02B 23/2484 600/109 |
| 2013/0137925 A1* | 5/2013 | Ushijima | A61B 1/0676 600/109 |
| 2013/0344456 A1* | 12/2013 | Jessop | A61C 19/004 433/29 |
| 2014/0073853 A1* | 3/2014 | Swisher | A61J 15/0026 600/104 |

(Continued)

*Primary Examiner* — Aaron B Fairchild
*Assistant Examiner* — Stephen Floyd London

(57) ABSTRACT

A disposable integrated endoscope integrates two light-emitting diodes (LED) and two CMOS image sensors on the front end of the endoscope, which not only can avoid the use of expensive light-guide prisms, be made as a relatively inexpensive and disposable integrated endoscope, but also provide a clearer 3D image of the internal tissues or organs of human body by means of the light emitted by the LEDs. In addition, by furnishing a heat dissipation structure having a heat-pipe at the front end of the endoscope, the high heat generated by the image sensors at the front end of the endoscope can be quickly dissipated to the rear end of the endoscope to achieve a good heat dissipation effect, so as to avoid scalding human tissues due to the temperature of the front end of the endoscope reaches 48° C. or above.

11 Claims, 12 Drawing Sheets

(56) References Cited

U.S. PATENT DOCUMENTS

| | | | |
|---|---|---|---|
| 2015/0250572 A1* | 9/2015 | Gramann | A61C 19/004 |
| | | | 433/29 |
| 2019/0056583 A1* | 2/2019 | Kuhn | G02B 23/2461 |
| 2019/0320879 A1* | 10/2019 | Langell | A61B 1/00057 |
| 2020/0375437 A1* | 12/2020 | Geafer | A61B 1/05 |
| 2020/0405140 A1* | 12/2020 | Lin | A61B 1/00172 |
| 2021/0220014 A1* | 7/2021 | Gitelis | A61B 17/3474 |
| 2021/0345868 A1* | 11/2021 | Fu | A61B 1/00066 |
| 2022/0142455 A1* | 5/2022 | Chen | A61B 1/042 |

* cited by examiner

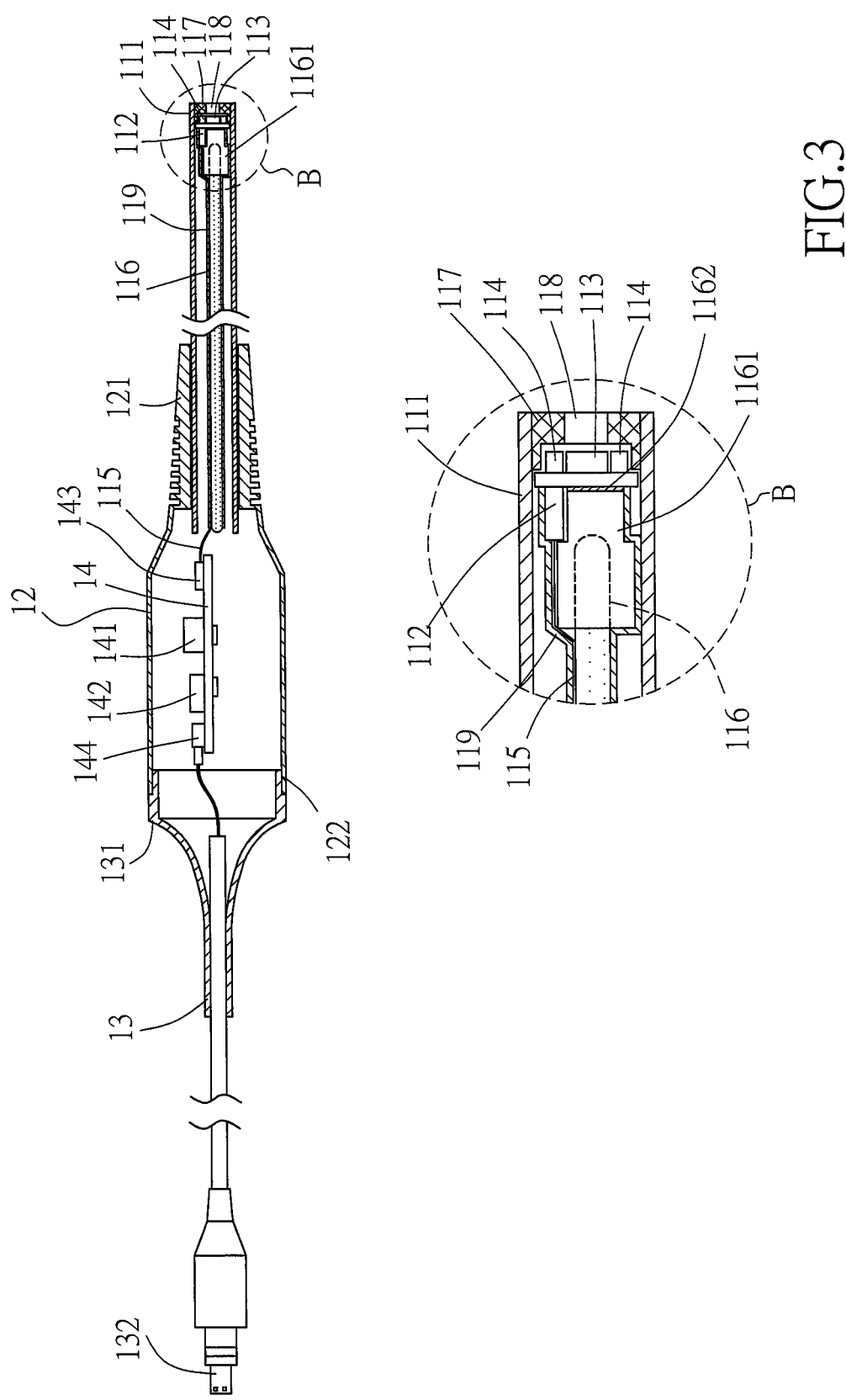

A-A Sectional View

DISPOSABLE INTEGRATED ENDOSCOPE

This application claims the benefit of Taiwan Patent Application Serial No. 109134233, filed Sep. 30, 2020, the subject matter of which is incorporated herein by reference.

BACKGROUND OF INVENTION

1. Field of the Invention

The present invention refers to a disposable integrated endoscope, especially refers to a disposable integrated endoscope that integrates image sensors and related circuitries into the endoscope, and is made as a relatively inexpensive and disposable integrated endoscope for one-time use.

2. Description of the Prior Art

Minimally invasive surgery using endoscopic vision has become a trend in surgery because of its advantages of minimal invasion, small wound, less bleeding, minimal damage to healthy tissues, and quick recovery. Typically, resection lesions can be achieved by endoscopic surgery with several small wounds, approximately one centimeter long. Therefore, wound pain of the patients is relieved by reducing the wound area. The recovery time and the number of hospitalization days are shortened.

Generally speaking, an endoscopic surgery system comprises an endoscope, a display device for showing the image captured by the endoscope, a processor for managing image signals, and surgery tools and instruments for operating the surgery. However, conventional endoscopic surgery system has the following deficiencies and thus is required for further improvements: (1) the conventional endoscope includes a prismatic light guide apparatus to guide image light from its front tip to the image capturing sensor located at the rear end of endoscope, the prismatic light guide apparatus is complex in structure and is expensive; (2) the conventional endoscope uses a charge-coupled device (CCD) to be the image capturing sensor, and thus requires additional analog-to-digital (A/D) converter to transform analog signals of CCD into digital signals, the A/D converter will cause image distortion and occupy additional volume; (3) due to high cost, the conventional endoscope is non-disposable and thus results in possible infection even though the endoscope is sterilized after use; (4) the conventional endoscope can only capture two-dimensional (2D) images, and therefore the image of three-dimensional (3D) tissues or organs is captured by the conventional endoscope and shown on the display in a 2D manner, and thus makes it more difficult for the medical personnel to positioning real points of the captured image while conducting the surgery; (5) although some manufacturers have tried to develop products with image sensor installed in the front end of the endoscope, however, they failed to stuff both the light source and the image sensor into the tiny front end of endoscope; in addition, they also failed to resolve the problem of high heat generated during the operation of the image sensor which will increase the temperature of the front end of endoscope to above 48° C. in a short period of time and will burn human tissues, and thus failed to comply with the safety regulations of electrical medical equipment; therefore, no such products have been used in the industry so far.

Accordingly, the present invention discloses a disposable integrated endoscope, which can solve various deficiencies of the aforementioned conventional endoscopes.

SUMMARY OF THE INVENTION

The primary objective of the invention is to provide a disposable integrated endoscope which can integrate the LED and image sensor on the front end of the endoscope, avoid the use of expensive light-guide prisms, and be made as a relatively inexpensive and disposable integrated endoscope. In addition, by furnishing a heat dissipation structure having a heat-pipe at the front end of the endoscope, the high heat generated by the image sensor at the front end of the endoscope can be quickly dissipated to the rear end of the endoscope to achieve a good heat dissipation effect, so as to avoid the temperature of the front end of the endoscope from reaching 48° C. or above.

Another objective of the invention is to provide a disposable integrated endoscope that, by furnishing two LEDs and two image sensors on the front end of the endoscope, not only the 3D images of the internal tissues or organs of human body can be captured, but also these captured 3D images can be even clearer by means of the light emitted by the LEDs.

In order to achieve the aforementioned objectives, the present invention discloses a disposable integrated endoscope, which comprises: an image capturing module, a handle, an image-transmission circuit board, and a cable module. The image capturing module is for capturing images and further comprises: a hollow outer tube, at least one image sensor, at least one light-supplying component such like light-emitting diode (LED), a flexible circuit board, and a heat-pipe. The hollow outer tube, extends a first length along a first direction and has a front end opening and a rear end opening. The at least one image sensor is located in the outer tube and adjacent to the front end opening. The image sensor is able to capture images of an object outside the front end opening and generate image signals accordingly. The at least one LED is located in the outer tube and adjacent to the image sensor near the front end opening. The LED is able to emit light to illuminate the object located outside the front end opening. The flexible circuit board is shaped like an elongated thin strip and received inside the outer tube. A front end of the flexible circuit board is electrically connected to the at least one image sensor and the at least one LED. A rear end of the flexible circuit board extends along the first direction and extends out of the rear end opening of the outer tube. The heat-pipe is accommodated in the outer tube and extends along the first direction for a second length. A front end of the heat-pipe is close to the at least one image sensor and the at least one LED, while a rear end of the heat-pipe is located near the rear end opening of the outer pipe. The heat-pipe is able to conduct a heat generated by the at least one image sensor and the at least one LED to a vicinity of the rear end opening of the outer pipe in order to provide a heat dissipation function. The handle is connected to a rear portion of the outer tube of the image capturing module. The handle has an inner compartment. The image-transmission circuit board is located within the inner compartment of the handle and is provided with a control unit which includes at least one integrated-circuit component capable of processing said image signals. The rear end of the flexible circuit board is electrically connected to the image-transmission circuit board. The image signals generated by the at least one image sensor are transmitted to the image-transmission circuit board via the flexible circuit board. The at least one integrated-circuit component included in the control unit is able to convert the image signals into digital signals that can be processed by a computer. The cable module is connected to the handle and includes a quick-coupling connector and a circuit board connector electrically connected to the quick-coupling connector. The quick-coupling connector is able to connect with a rear-end device. The circuit board connector is electrically connected to the image-transmission circuit board, so that the digital signal converted by the control unit can be transmitted to the rear-end device via the quick-coupling connector of the cable module, in addition, the rear-end device can also provide power to the image-transmission circuit board via the cable module.

In a preferred embodiment, the disposable integrated endoscope further comprises: a chip carrier, a front cover, a protective glass, a heat-pipe stand, and a first connector. The chip carrier is located in the outer tube and adjacent to the front end opening. The chip carrier has a carrying surface perpendicular to the first direction and a rear surface opposite to the carrying surface. A circuit layout is provided on the chip carrier. The at least one image sensor is disposed on the carrying surface and electrically connected to the circuit layout of the chip carrier. The at least one LED is disposed on the carrying surface and electrically connected to the circuit layout of the chip carrier. The front cover covers the carrying surface of the chip carrier. The front cover is respectively provided with an opening at positions corresponding to the at least one image sensor and the at least one LED, such that a light-sensing surface of the image sensor and a light-emitting surface of the LED can be respectively plugged into the corresponding openings and exposed to a front surface of the front cover. The front cover is plugged and fixed at the front end opening of the outer tube, such that the chip carrier together with the at least one image sensor and the at least one LED thereon can be fixed to the front end opening of the outer tube by means of the front cover. The flexible circuit board is electrically connected to the circuit layout of the chip carrier. The protective glass covers the front surface of the front cover and corresponding to the light-sensing surface of the image sensor. The heat-pipe stand caps on a front end of the heat-pipe. An outer diameter of the heat-pipe stand is approximately equal to or slightly smaller than an inner diameter of the outer tube. The heat-pipe stand positions and supports the front end of the heat-pipe at a location close to the front end opening of the outer tube. The heat-pipe stand has a front end surface. A thermal tape is provided on the front end surface of the heat-pipe stand. The thermal tape is attached and sandwiched between the front end surface of the heat-pipe stand and the rear side surface of the chip carrier, such that a heat generated by the at least one image sensor and the at least one LED can be quickly and effectively dissipated to the heat-pipe stand and the heat-pipe via the chip carrier and the thermal tape. The first connector is furnished at the rear end of the flexible circuit board away from the chip carrier. The first connector is connected with a connector socket of the image-transmission circuit board.

In a preferred embodiment, the image capturing module further comprises a heat-shrinkable sleeve which covers outside of the heat-pipe, the heat-pipe stand and part of the flexible circuit board. By heating the heat-shrinkable sleeve, the heat-shrinkable sleeve can be shrunk; such that the flexible circuit board can attach on an outer surface of the heat-pipe.

In a preferred embodiment, the number of the at least one LED is two, and these two LEDs are respectively located on upper and lower sides of the at least one image sensor.

In a preferred embodiment, the number of the at least one image sensor is two, and these two image sensors are adjacently arranged in a left and right side-by-side manner, and said two image sensors are both located between the two LEDs.

In a preferred embodiment, an indicator is arranged on an outer surface of the handle; the indicator indicates a position where a rotation angle of the image sensor is 0 degrees.

In a preferred embodiment, the image sensor is Complementary Metal Oxide Semiconductor (CMOS) image sensor. The image signals generated by the image sensor are directly transmitted via the circuit layout on the chip carrier to the flexible circuit board and then further directly transmitted to the image-transmission circuit plate. The control unit on the image-transmission circuit board provides functions that comply with the Mobile Industry Processor Interface (MIPI) specifications, which can convert the image signals from the at least one image sensor into the digital signals that can be processed by the computers.

In a preferred embodiment, the digital signals converted and generated by the control unit of the image-transmission circuit board comply with one of the following specifications: high-definition multimedia interface (HDMI) specification, DisplayPort (DP) specification, video graphics interface (VGA) specification, Digital Visual Interface (DVI) specification, or Universal Serial Bus (USB) specification.

In a preferred embodiment, the at least one light-supplying component includes a bunch of optical fibers. The optical fibers are furnished inside the disposable integrated endoscope and extending between an optical-fiber connector furnished on the handle and the chip carrier. Front ends of the optical fibers are arranged and distributed to surround on an outer periphery of the at least one image sensor. Such that, the light rays emitted out from these optical fibers can provide an even and clear illumination effect for the external objects such as the internal tissues or organs of the human body.

BRIEF DESCRIPTION OF THE DRAWINGS

The present invention will now be specified with reference to its preferred embodiment illustrated in the drawings, in which:

FIG. 3 is a schematic cross-sectional view of the embodiment of the disposable integrated endoscope of the present invention;

DESCRIPTION OF THE PREFERRED EMBODIMENT

The invention discloses a disposable integrated endoscope, which integrates two light-emitting diodes (LED) and two CMOS image sensors on the front end of the endoscope, which not only can avoid the use of expensive light-guide prisms, be made as a relatively inexpensive and disposable integrated endoscope, but also provide a clearer 3D image of the internal tissues or organs of human body by means of the light emitted by the LEDs. In addition, by furnishing a heat dissipation structure having a heat-pipe at the front end of the endoscope, the high heat generated by the image sensors at the front end of the endoscope can be quickly dissipated to the rear end of the endoscope to achieve a good heat dissipation effect, so as to avoid scalding human tissues due to the temperature of the front end of the endoscope reaches 48° C. or above.

In order to more clearly describe the disposable integrated endoscope of the present invention, preferred embodiments will be illustrated in detail accompanied by drawings.

Figure 1:
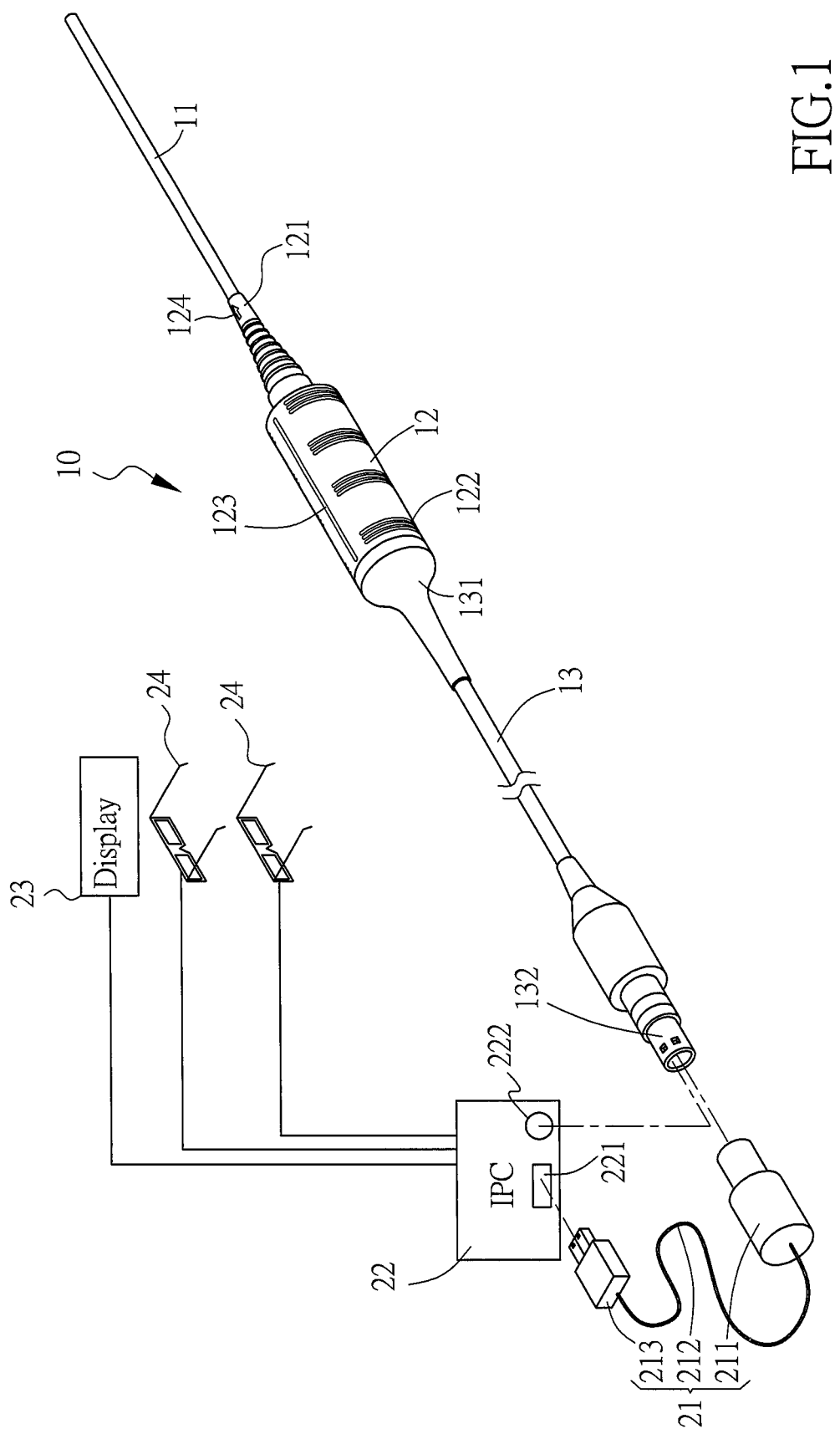
FIG. 1 is a three-dimensional assembly view of an embodiment of the disposable integrated endoscope of the present invention.
Figure 2:
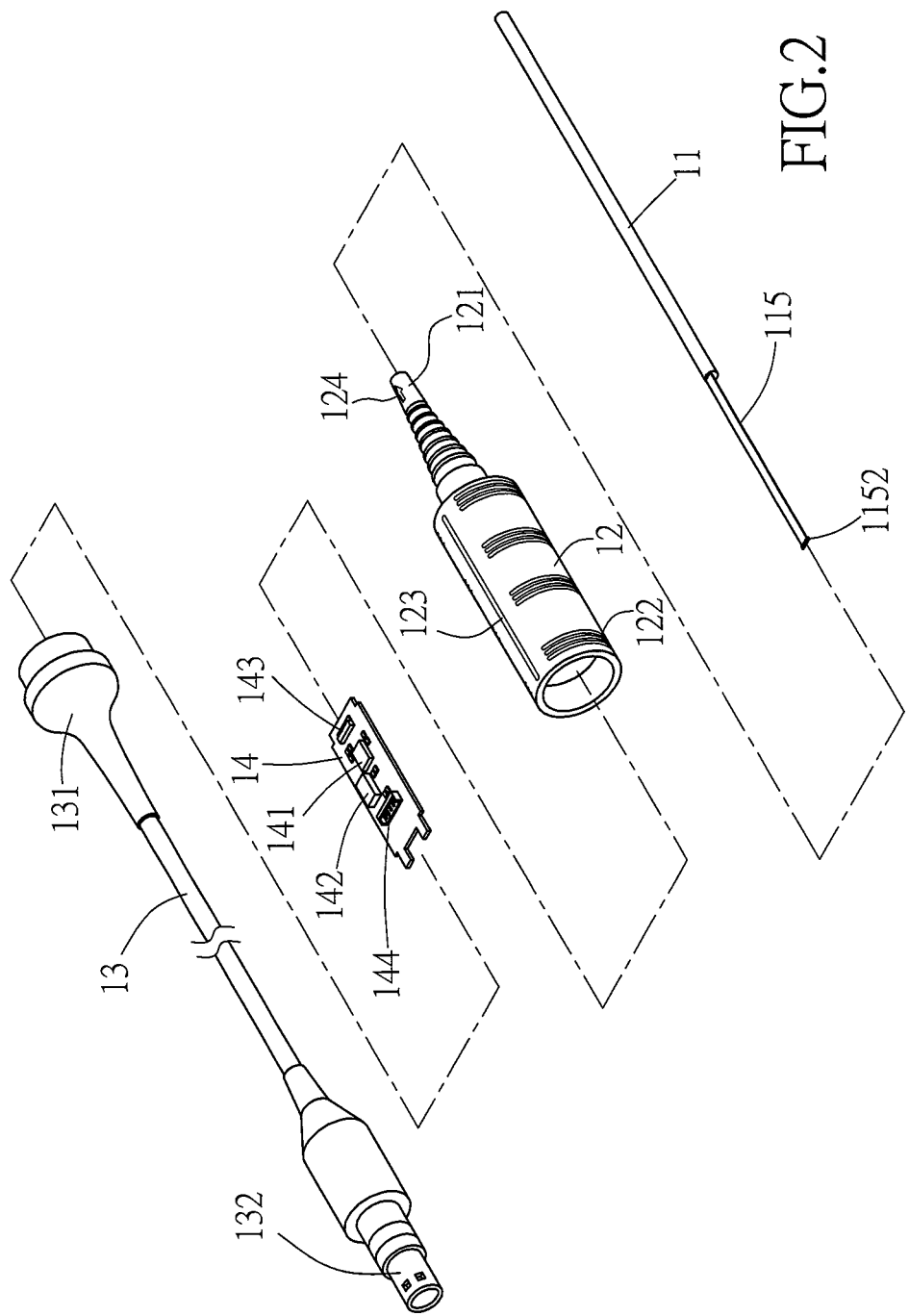
FIG. 2 is a three-dimensional exploded view of the embodiment of the disposable integrated endoscope of the present invention.

Please refer to FIG. 1, FIG. 2 and FIG. 3, which respectively are the three-dimensional assembly view, the three-dimensional exploded view, and the schematic cross-sectional view of an embodiment of the disposable integrated endoscope of the present invention. In the present invention, the disposable integrated endoscope 10 is suitable for performing minimally invasive endoscopic surgery, especially for minimally invasive endoscopic surgeries related to orthopedics, joints, spine, skull and brain. The medical staff can operate the endoscope 10 to enter the patient's body through a small wound in order to approach the surgical target (such as human tissue or organ). The images of the surgical target captured by the endoscope can be transmitted to an external device, for example, a medical industrial personal computer (IPC) 22 (also referred as control host hereinafter) through a rear-end device 21 connected to the rear end of the endoscope 10. And then, through the IPC 22, the images of the surgical target are processed, stored and further transmitted to one or more display devices 23, 24. The display devices 23, 24 are connected to the IPC 22 in a wired or wireless communication manner for receiving image signals therefrom. The display devices 23, 24 receive and decode the image signals from the IPC 22 and then display the images on the display devices 23, 24 in either a two-dimensional (2D) or three-dimensional (3D) manner. In this embodiment, the display devices 23, 24 can be a naked-eye 3D display (23) or a smart-glasses (24). When the display device 24 is the smart-glasses, the medical personnel can wear such smart-glasses and watch the images acquired by the endoscope 10 in a 3D virtual reality manner, such like, but not limited to: Virtual Reality (VR), Augmented Reality (AR), or Mixed Reality (MR). When the display device 23 is the naked-eye 3D display, it can be fixed on the wall or other places for other medical personnel to watch with bare-eyes without wearing the smart-glasses. In another embodiment, the display device 23 can also be the ordinary 2D display monitors, which can display the images in a 2D manner. By watching the 3D images of the surgery target shown on either the smart-glasses or the naked-eye 3D display, the medical personnel can easily, steadily and precisely operate the medical tool and/or medical instruments to perform the minimally invasive endoscopic surgery. The IPC 22 can be further connected with other external devices or other display devices. The external devices can be ordinary or commonly used medical instruments, such as, but not limited to, surgical lamp machine, electrocardiographic machine, bipolar radio-frequency (RF) machine, cold light providing machine, power providing machine, etc.

As shown in FIG. 1 to FIG. 3, in this embodiment, the disposable integrated endoscope 10 of the invention comprises: an image capturing module 11, a handle 12 connected to the rear end of the image capturing module 11, a cable module 13 connected to the rear end of the handle 12, and an image-transmission circuit board 14 furnished inside the handle 12. The disposable integrated endoscope 10 is furnished with a quick-coupling connector 132 at the end of the cable module 13 for connecting to the external device. In a preferred embodiment of the invention, the quick-coupling connector 132 can be matched and connected to another corresponding quick-coupling connector 222 provided on the IPC 22. In this case, the external device is the IPC 22. Such that, the digital image signals generated by the disposable integrated endoscope 10 can be transmitted to the IPC 22 through these two connected quick-coupling connectors 132 and 222 for further signal processing, distribution and storage. In another embodiment, the quick-coupling connector 132 can also be matched and assembled with another corresponding quick-coupling connector 211 of the rear-end device 21. In this case, the external device is the rear-end device 21. Such that, the digital image signals generated by the disposable integrated endoscope 10 can be transmitted to the rear-end device 21 through these two corresponding quick-coupling connectors 132 and 211 connected to each other. After the control unit installed inside the rear-end device 21 converts the image signal into another digital signal conforming to the universal serial port (USB) protocol, the converted digital signal is then sent to the IPC 22 for further signal processing, distribution and storage via the cable 212 and the USB plug 213 of the back-end device 21 plugged to the USB socket 221 of the IPC 22. Because USB protocol is a common protocol, the rear-end device 21 allows the image signals generated by the disposable integrated endoscope 10 of the present invention to be transmitted to various IPCs with USB sockets. The disposable integrated endoscope 10 of the present invention is designed as an integrated and disposable product. Once the minimally invasive endoscopic surgery is completed, the used endoscope 10 can be discarded readily by simply separating the two quick-coupling connectors 132 and 211 in order to replace it with a new disposable integrated endoscope 10, and thus can avoid cross infection.

Figure 4A:
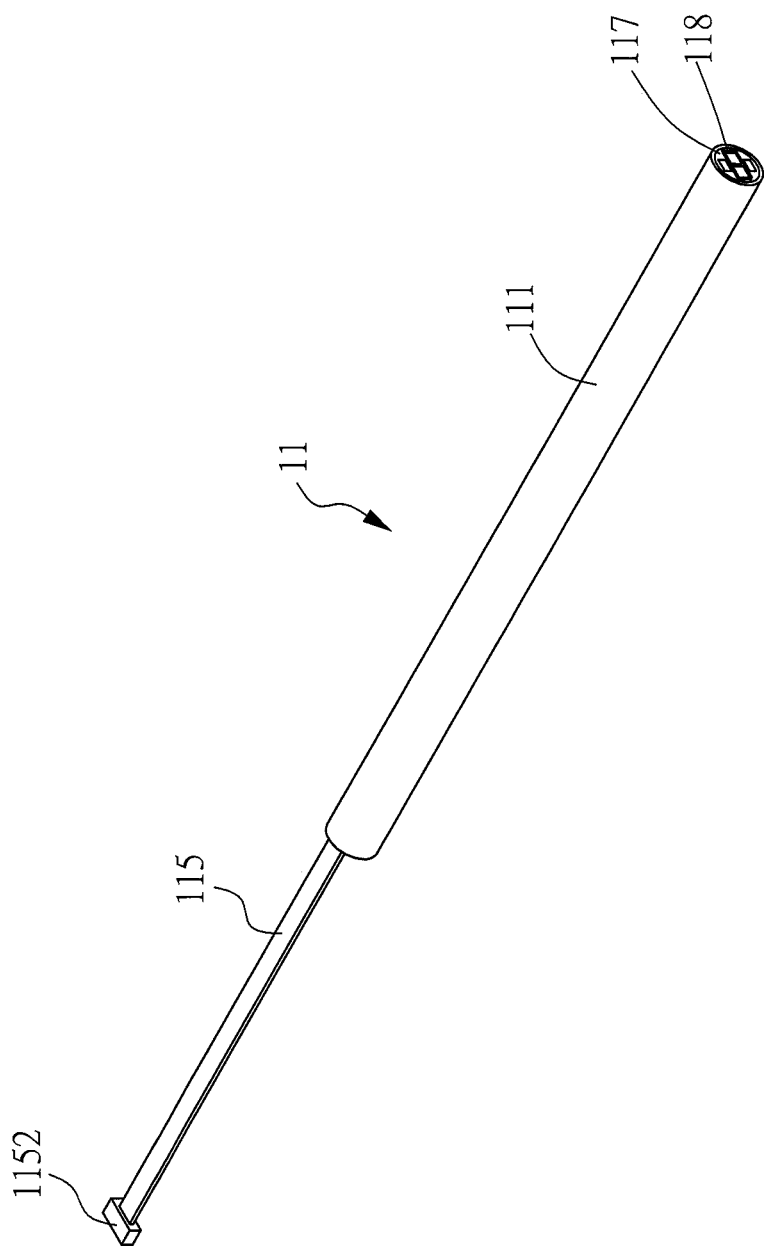
FIG. 4A and FIG. 4B are respectively a three-dimensional schematic diagram and a three-dimensional exploded view of an embodiment of the image capturing module of the disposable integrated endoscope of the present invention.
Figure 4B:
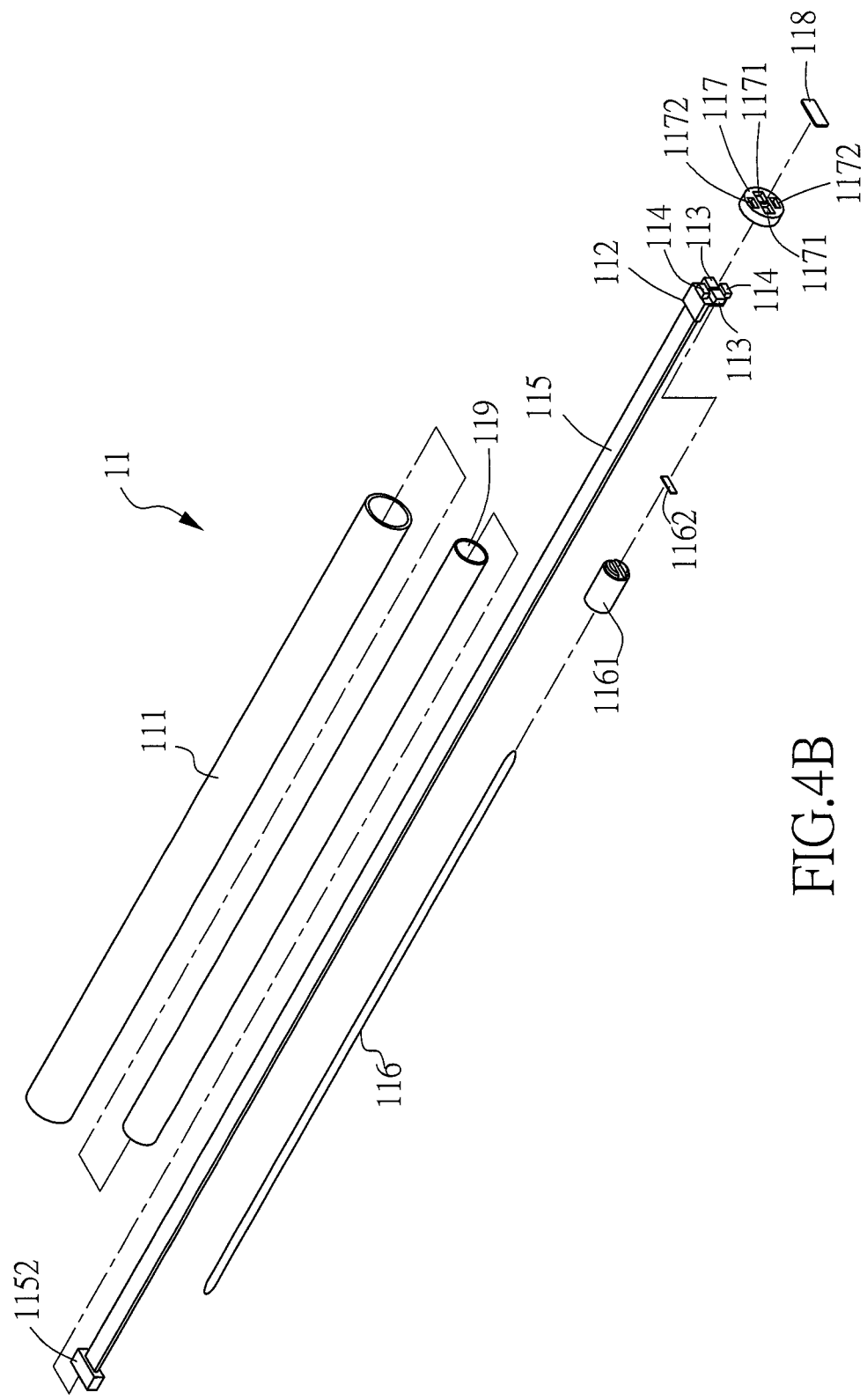

Please refer to FIG. 4A and FIG. 4B, which are respectively a three-dimensional schematic diagram and a three-dimensional exploded view of an embodiment of the image capturing module of the disposable integrated endoscope of the present invention. The dotted area marked with B in the lower half of FIG. 3 is a partially enlarged view of the dotted area also marked with B in the upper half of FIG. 3. As shown in FIG. 3, FIG. 4A and FIG. 4B, in an embodiment of the disposable integrated endoscope 10 of the present invention, the image capturing module 11 provides the function of capturing images and comprises: a hollow outer tube 111, a chip carrier 112, at least one image sensor 113, at least one light-supplying component 114, a flexible circuit board 115, a heat-pipe 116, a heat-pipe holder 1161, a front cover 117, a protective glass 118, and a heat-shrinkable sleeve 119. In this embodiment, the light-supplying component is light-emitting diode (LED) 114. The hollow outer tube 111 is made of rigid and inflexible material, for example, but not limited to: stainless steel or titanium alloy, etc.; such material meets the requirements of ISO10993 biological compatibility. The outer tube 111 is an elongated thin tube, which extends a first length along a first direction, and has a front end opening and a rear end opening. In a preferred embodiment, the length of the outer tube 111 is between 8 cm and 20 cm, the outer diameter thereof is between 2 mm and 10 mm, and the thickness of the tube wall is between 0.01 mm and 0.04 mm. If the length of the outer tube 111 is too long (say, more than 20 cm), then it is easy to cause noise or distortion of the signal of the CMOS image sensor 113 due to the long transmission distance. If the outer diameter of the outer tube 111 is too large (say, more than 12 mm), then the wound of the patient will be enlarged. The at least one image sensor 113 is located in the outer tube 111 and adjacent to the front end opening, which is used to capture the images of an object outside the front end opening and generate image signals accordingly. The at least one LED 114 is located in the outer tube 111 at a location adjacent to the image sensor 113 close to the front end opening, and is used to emit light to illuminate the object located outside the front end opening. The chip carrier 112 is located in the outer tube 111 and adjacent to the front end opening, and has a carrying surface (also referred to as a front surface) perpendicular to the first direction and a rear surface opposite to the carrying surface. A circuit layout is provided on the chip carrier 112. The at least one image sensor 113 is disposed on the carrying surface and electrically connected to the circuit layout of the chip carrier 112. In addition, the at least one LED 114 is also disposed on the carrying surface and electrically connected to the circuit layout of the chip carrier 112. In this embodiment, the number of the at least one LED 114 is two, and these two LEDs 114 are respectively located on the upper and lower sides of the at least one image sensor 113. Moreover, the number of the at least one image sensor 113 is also two, and these two image sensors 113 are adjacently arranged in a left and right side-by-side manner, and both are located between the two LEDs 114 along a vertical direction. In this embodiment, these two image sensors 113 are arranged side-by-side adjacent to each other on the carrying surface of the chip carrier 112 which is located near the front end opening of the endoscope 11; in addition, these two image sensors 113 are both Complementary Metal Oxide Semiconductor (CMOS) image sensors with a resolution of at least 1280×720 pixels. In other words, the resolution of the combination of these two adjacently arranged image sensors 113 is at least 2560× 720 pixels. With two CMOS image sensors 113 adjacently arranged in the left and right side-by-side manner, it is possible to capture clear and visible 3D images of external objects (such as internal tissues or organs of the human body) within a parallax range of 0.5 mm to 100 mm in distance and 0.8 degrees to 8 degrees in angle, and convert the captured 3D images into digital image signals. Therefore, there is no need to furnish an analog-to-digital converter (A/D Converter) on the chip carrier 112 at the front end opening of the outer tube 111, so the outer diameter of the front end opening of the outer tube 111 of endoscope 11 can be greatly reduced. Furthermore, the two LEDs 114 are disposed on the front carrying surface of the chip carrier 112 and are respectively located on the upper and lower sides of the two image sensors 113. The two LEDs 114 can emit light toward the external objects from both the upper and lower sides of the image sensors 113; such novel arrangement not only can help the two image sensors 113 to obtain clearer images of the internal tissues or organs of the human body, but also avoid the occurrence of dark shadows.

The flexible circuit board 115 is in a shape of elongated thin strip and is received inside the outer tube 111. A front end of the flexible circuit board 115 is connected to the chip carrier 112 and also electrically connected to the circuit layout, and thus further electrically connected to the image sensors 113 and the LEDs 114 via the circuit layout. A rear end of the flexible circuit board 115 extends along the first direction and extends out of the rear end opening of the outer tube 111 by an appropriate length. The first connector 1152 is furnished at the rear end of the flexible circuit board 115 away from the chip carrier 112; and, the first connector 1152 is used to connect to a connector socket 143 of the image-transmission circuit board 14.

The heat-pipe 116 is accommodated in the outer tube 111 and extends along the first direction for a second length. The second length of the heat-pipe 116 is approximately equal to the first length of the outer tube 111. A front end of the heat-pipe 116 is close to the image sensors 113 and the LEDs 114, and a rear end of the heat-pipe 116 is located near the rear end opening of the outer pipe 111. The heat-pipe 116 can conduct the heat generated by the image sensors 113 and the LEDs 114 to the vicinity of the rear end opening of the outer pipe 111 in order to provide a heat dissipation function. The disposable integrated endoscope 10 of the present invention further includes a novel cap-like heat-pipe stand 1161, capped (set) on the front end of the heat-pipe 116. An outer diameter of the heat-pipe stand 1161 is approximately equal to or slightly smaller than an inner diameter of the outer tube 111, and can provide the function of positioning and supporting the front end of the heat-pipe 116 at a location close to the front end opening of the outer tube 111. The heat-pipe stand 1161 has a front end surface; and, a thermal tape 1162 is provided on the front end surface of the heat-pipe stand 1161. The thermal tape 1162 is attached and sandwiched between the front end surface of the heat-pipe stand 1161 and the rear side surface of the chip carrier 112, such that the heat generated by the at least one image sensor 113 and the at least one LED 114 can be quickly and effectively dissipated (transmitted) to the heat-pipe stand 1161 and the heat-pipe 116 via the chip carrier 112 and the thermal tape 1162. Such novel design not only greatly improves the heat dissipation effect of the heat-pipe 116, but also combines the heat-pipe 116, the chip carrier 112 and the image sensors 113 and the LEDs 114 all together on the same heat-pipe stand 1161, such that all these components can be easily and rapidly positioned on the front end opening of the outer pipe 111. With this novel structural design of the heat-pipe 116 and the cap-like heat-pipe stand 1161, the temperature of the front end of the outer tube 111 of the endoscope 10 can always be kept below 48° C. under long time operation, even that there are two image sensors 113 and two LEDs 114 provided at the tinny front end of the outer tube 111, so there is no risk of scalding human tissues at all.

The front cover 117 covers the carrying surface of the chip carrier 112. The front cover 117 is respectively provided with an opening 1171 and 1172 at positions corresponding to the at least one image sensor 113 and the two LEDs 114; such that, the light-sensing surface of each of the image sensors 113 and the light-emitting surface of each of the LEDs 114 can be respectively plugged into the corresponding openings 1171 and 1172 and exposed to a front surface of the front cover 117. In addition, the front cover 117 is plugged and fixed at the front end opening of the outer tube 111, such that the chip carrier 112 together with the image sensors 113 and the LEDs 114 thereon can be fixed to the front end opening of the outer tube 111 by means of the front cover 117. The protective glass 118 covers the front surface of the front cover 117 and corresponds to the light-sensing surface of the at least one image sensor 113. In the present invention, the materials of the outer tube 111, the protective glass 118, and the front cover 117 of the image capturing module 11 all meet the ISO10993 biological compatibility requirements.

Figure 5B:
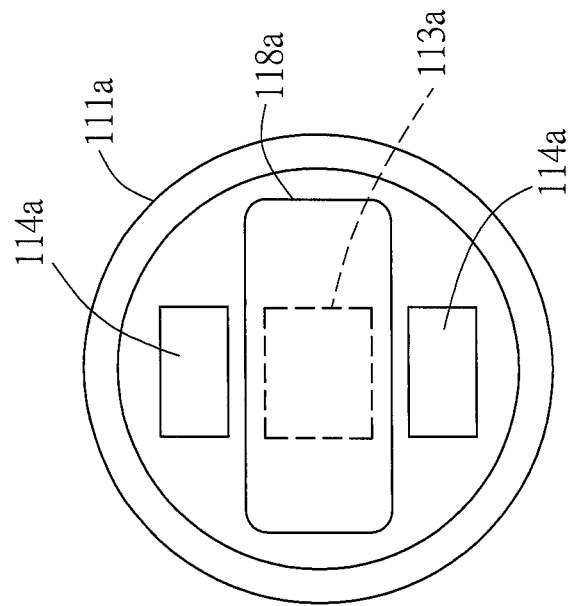
FIG. 5A and FIG. 5B are schematic diagrams of two different embodiments of the front end surface of the outer tube of the image capturing module of the disposable integrated endoscope in accordance with the present invention.
Figure 5A:
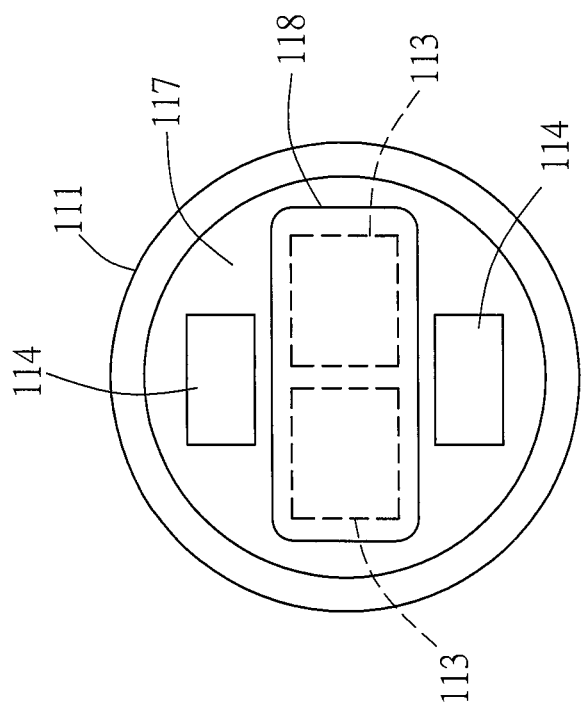

Please refer to FIG. 5A and FIG. 5B, which are schematic diagrams of two different embodiments of the front end surface of the outer tube 111 of the image capturing module 11 of the disposable integrated endoscope 10 in accordance with the present invention. As shown in FIG. 5A, when the disposable integrated endoscope 10 of the present invention includes two image sensors 113 arranged adjacent to each other in a left-and-right side-by-side manner in order to capture 3D images, because there are two image sensors 113 and two LEDs 114 to be provided at the front end opening of the outer tube 111, the outer diameter of the outer tube 111 is approximately between 5 mm and 10 mm. As shown in FIG. 5B, when the disposable integrated endoscope 10 of the present invention includes only one image sensor 113 (covered by the protective glass 118a) and two LEDs 114 for capturing 2D images, because there are fewer components, the outer diameter of the outer tube 111a is approximately between 3 mm and 6 mm. It is notable that, no matter how many image sensors 113, 113a are included, at least two LEDs 114, 114a are respectively located on the upper and lower sides of the image sensor 113, 113a for providing lighting function, which not only can help the image sensor 113, 113a to obtain clearer images of the internal tissues or organs of the human body, but also can avoid the occurrence of dark shadows.

Figure 6A:
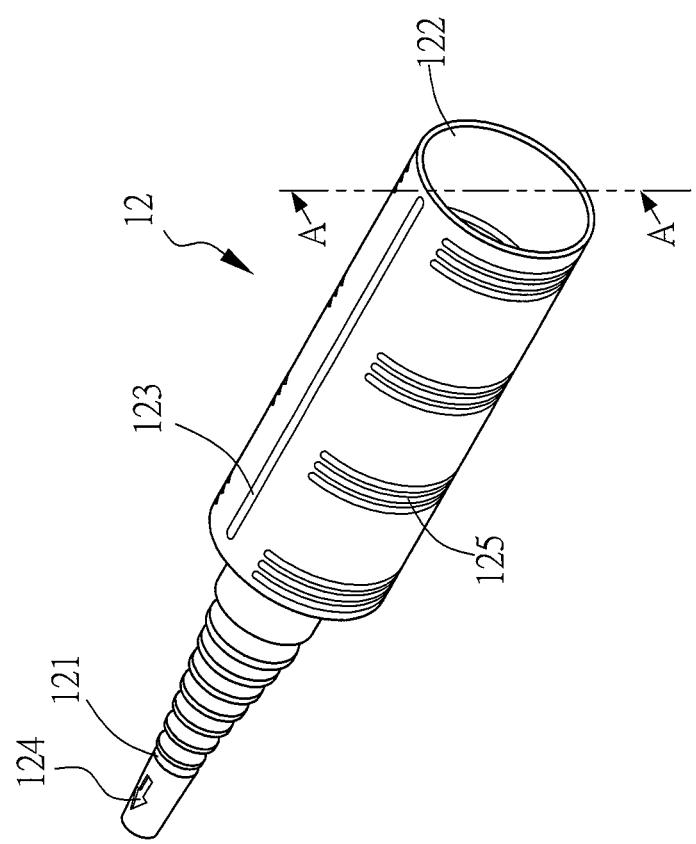
FIG. 6A and FIG. 6B are respectively a three-dimensional view and A-A cross-sectional view of an embodiment of the handle of the disposable integrated endoscope of the present invention.
Figure 6B:
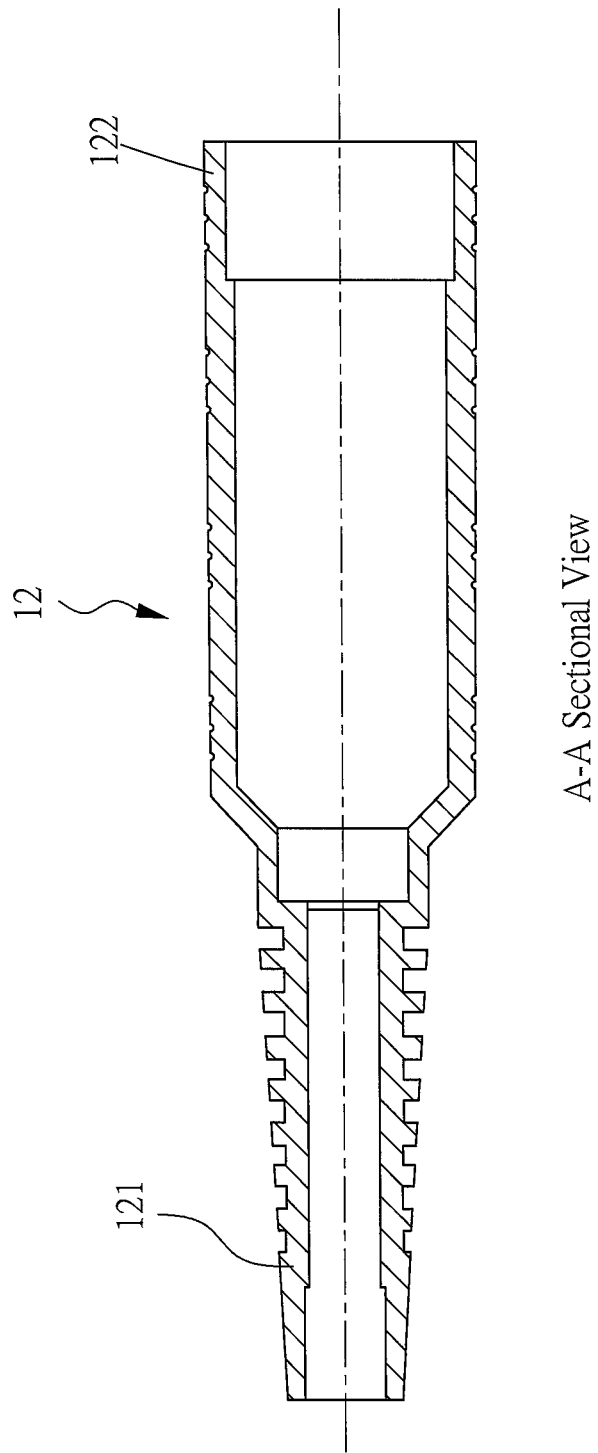

Please refer to FIG. 6A and FIG. 6B, which are respectively a three-dimensional view and A-A cross-sectional view of an embodiment of the handle of the disposable integrated endoscope of the present invention. In this embodiment, the handle 12 is connected to the rear portion of the outer tube 111 of the image capturing module 11, and is used as a handle for the user to hold by hand or grab by tools. The handle 12 is made of medical plastic that meets ISO10993 biocompatibility conditions. The handle 12 has an inner compartment, a front-end portion 121 for connecting the outer tube 111 of the image capturing module 11, and a rear-end portion 122 for connecting the cable module 13. The outer surface of the handle 12 is provided with a plurality of ring-shaped bulged anti-skid structures 125. The present invention further includes a novel design that an indicator line 123 or (and) an indicator 124 extending along the first direction is arranged on the outer surface of the handle 12; wherein, the indicator line 123 or (and) the indicator 124 indicates the position where the rotation angle of the image sensor 113 is 0 degrees. That means, the indicator line 123 or (and) the indicator 124 indicates the position (angle) at six o'clock facing the surgeon. Therefore, when the surgeon (user) operates the disposable integrated endoscope 10 of the present invention, he/she only needs to observe the position of the indicator line 123 or (and) the indicator 124 on the outer surface of the handle 12 to understand whether or not the filming angle of the captured images is rotated or skewed. The surgeon (user) can also operate and rotate the handle 12 in order to keep the indicator line 123 or (and) the indicator 124 directly at his/her six o'clock direction in front of his/her vision (that is, the position where the rotation angle is 0 degrees), which can ensure that the rotation angle of the object's images captured by the image sensor 113 is also 0 degrees without rotation. This can greatly improve the accuracy and safety of endoscopic minimally invasive surgery.

Figure 7:
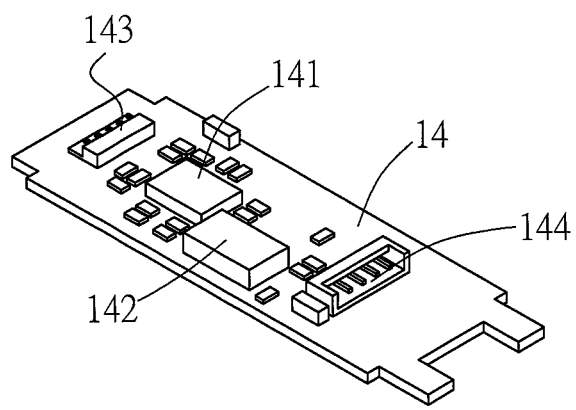
FIG. 7 is a three-dimensional schematic diagram of an embodiment of the image-transmission circuit board of the disposable integrated endoscope of the present invention.

Please refer to FIG. 7, which is a three-dimensional schematic diagram of an embodiment of the image-transmission circuit board of the disposable integrated endoscope of the present invention. The image-transmission circuit board 14 provides the function of relay processing of image signals and is located within the inner compartment of the handle. The image-transmission circuit board 14 is provided with a control unit (including at least one integrated-circuit component 141, 142 and a plurality of active and/or passive components) capable of processing image signals, and two connector sockets 143, 144. In a preferred embodiment, the integrated-circuit components 141, 142 include a Field Programmable Gate Array (FPGA) which is a semiconductor integrated circuit where electrical functionality is customized to accelerate key workloads, such as processing of image signals; in the meantime, an image signal processing (ISP) IC is furnished inside the IPC 22 for accepting and further processing the image signals processed by the FPGA. Such novel design has the advantages of higher processing efficiency and lower cost. However, in another embodiment of the invention, the integrated-circuit components 141, 142 of the image-transmission circuit board 14 may include the ISP IC only, or both the FPGA and the ISP IC. The rear end of the flexible circuit board 115 is plugged into the connector socket 143 at the front end of the image-transmission circuit board 14 through the first connector 1152, and thus is electrically connected to the image-transmission circuit board 14. The image signals generated by the at least one image sensor 113 can be transmitted to the image-transmission circuit board 14 via the flexible circuit board 115; and then, the at least one integrated-circuit component 141, 142 included in the control unit can convert the image signals into digital signals that can be processed by a computer. In the present invention, the digital image signals generated by the at least one image sensor 113 (CMOS image sensor) are directly transmitted via the circuit layout on the chip carrier 112 to the flexible circuit board 115 and then further directly transmitted to the image-transmission circuit plate 14. The control unit on the image-transmission circuit board 14 provides functions that comply with the Mobile Industry Processor Interface (MIPI) specifications, which can convert the digital image signals from the at least one image sensor 113 into the digital signals that can be processed by computers. Moreover, the digital signals converted and generated by the control unit of the image-transmission circuit board 14 comply with one of the following specifications: high-definition multimedia interface (HDMI) specification, DisplayPort (DP) specification, video graphics interface (VGA) specification, Digital Visual Interface (DVI) specification, or Universal Serial Bus (USB) specification.

Figure 8:
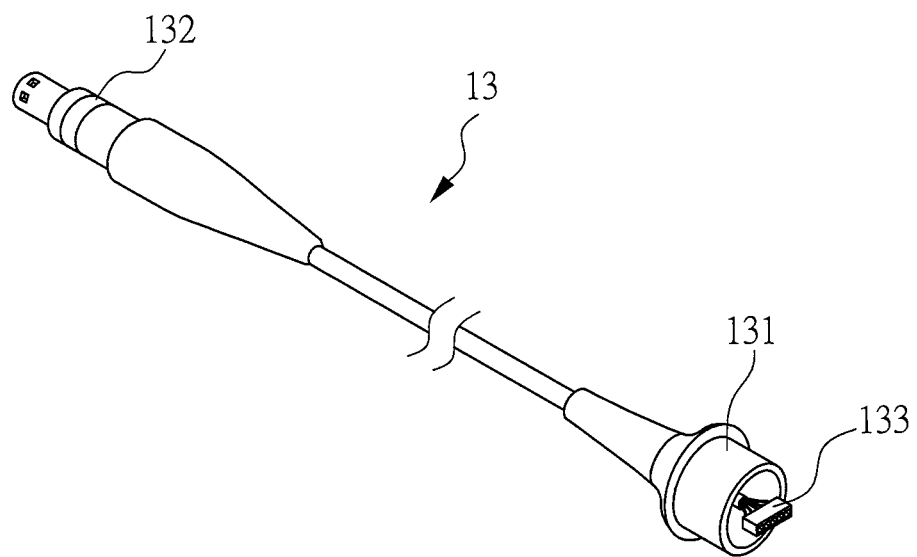
FIG. 8 is a perspective view of an embodiment of the cable module of the disposable integrated endoscope according to the present invention.

Please refer to FIG. 8, which is a perspective view of an embodiment of the cable module of the disposable integrated endoscope according to the present invention. The cable module 13 is connected to the handle 12 and the image-transmission circuit board 14 for transmitting the converted digital signals (image signals) to the rear-end device 21 and receiving power and control signals from the rear-end device 21. The material of the cable module 13 is medical plastic conforming to ISO10993 biocompatibility conditions. The cable module 13 comprises: a quick-coupling connector 132 located at the rear end of the cable module 13, and a circuit board connector 133 located at the front end 131 of the cable module 13, and a long and flexible cable extending there-between; wherein the circuit board connector 133 is electrically connected to the quick-coupling connector 132 through a cable. The quick-coupling connector 132 can be matched and connected with another quick-coupling connector 211 of the rear-end device 21 in a detachable manner. The circuit board connector 133 is plugged into the connector socket 144 at the rear end of the image-transmission circuit board 14 and therefore is electrically connected to the image-transmission circuit board 14, so that the digital signal converted by the control unit can be transmitted to the rear-end device 21 via the quick-coupling connector 133 of the cable module 13. In addition, the rear-end device 21 can also provide power to the image-transmission circuit board 14 via the cable module 13.

Please refer to FIG. 3 and FIG. 4B; in this embodiment, the disposable integrated endoscope 10 of the present invention further includes the heat-shrinkable sleeve 119 which covers at least the outside of the heat-pipe 116, the heat-pipe stand 1161 and part of the flexible circuit board 115. By heating the heat-shrinkable sleeve 119, the heat-shrinkable sleeve 119 can be shrunk; such that the flexible circuit board 115 will be pressed by the shrunk heat-shrinkable sleeve 119 and thus attaches on the outer surface of the heat-pipe 116. In this way, in addition to the heat-pipe 116, the heat-pipe stand 1161 and the flexible circuit board 115 can be tightly tied together to facilitate assembly, the flexible circuit board 115 can also be attached on the outer surface of the heat pipe 116. Therefore, the heat-pipe 116 can provide a good heat-dissipation function to the flexible circuit board 115, which further improves the heat-dissipation effect that the heat-pipe 116 can achieve for the image capture module 11.

Because most of the components of the embodiment described below are the same or similar to the previously described embodiments, therefore, the same or similar components will be given the same component names and numbers, and detailed descriptions thereof will not be repeated hereinafter.

Figure 9:
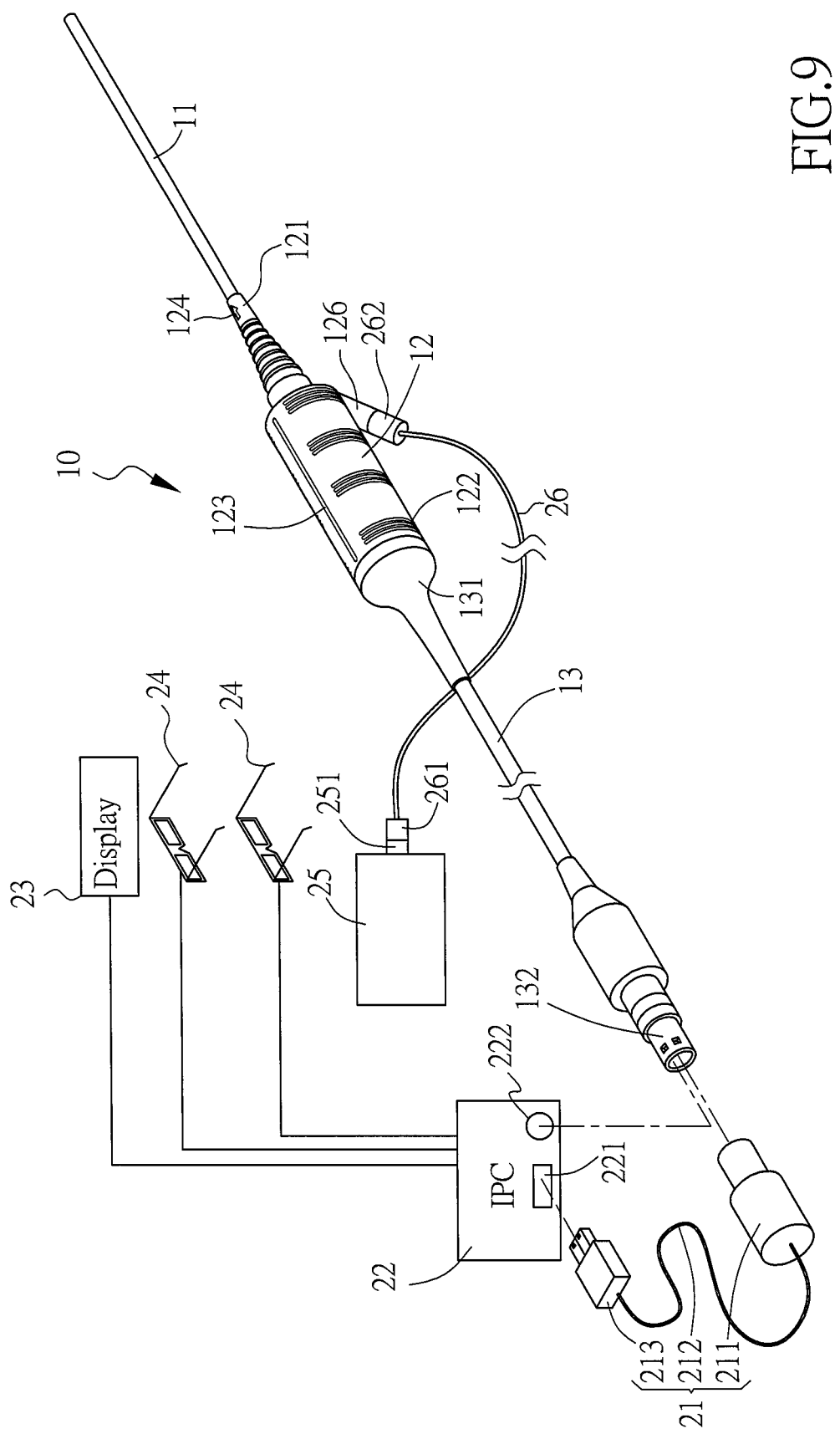
FIG. 9 is a three-dimensional assembly view of another embodiment of the disposable integrated endoscope of the present invention.
Figure 10:
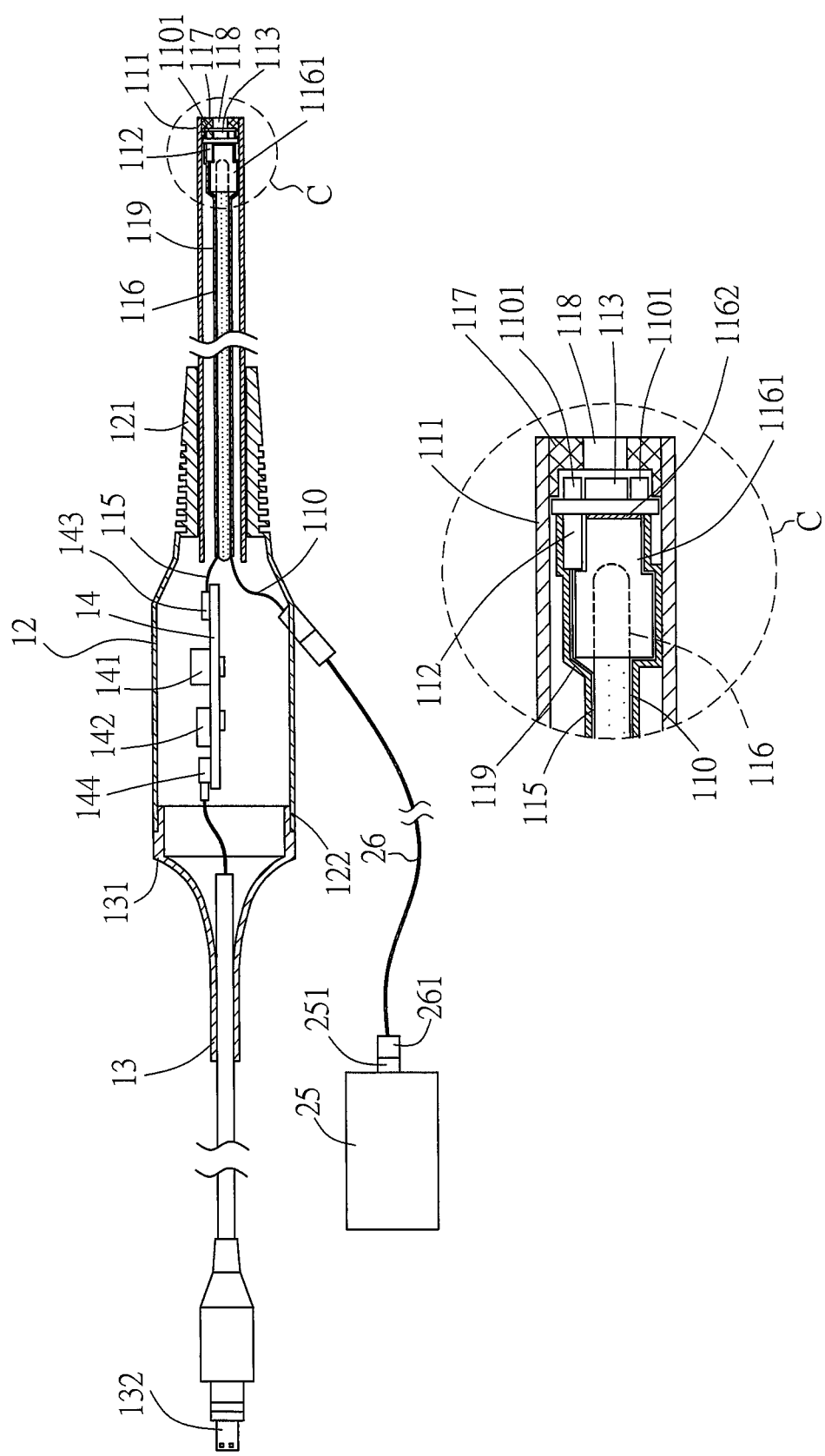
FIG. 10 is a schematic cross-sectional view of another embodiment of the disposable integrated endoscope of the present invention.
Figure 11:
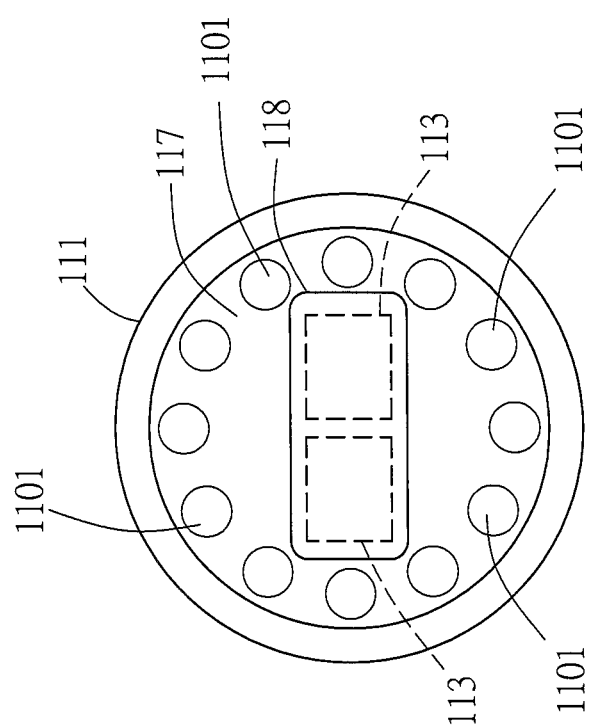
FIG. 11 is a schematic front-end view of another embodiment of the disposable integrated endoscope of the present invention.

Please refer to FIG. 9, FIG. 10 and FIG. 11, which respectively are the three-dimensional assembly view, the schematic cross-sectional view, and a schematic front-end view of another embodiment of the disposable integrated endoscope of the present invention. In this embodiment, the disposable integrated endoscope 10 of the invention comprises: an image capturing module 11, a handle 12 connected to the rear end of the image capturing module 11, a cable module 13 connected to the rear end of the handle 12, and an image-transmission circuit board 14 furnished inside the handle 12. The difference between the embodiment shown in FIGS. 9 to 11 and the previously described embodiment is that, instead of the LEDs, the disposable integrated endoscope 10 of this embodiment uses optical fibers to transmit light rays provided from an external light source to illuminate the object located outside the front end opening of the outer tube 111. That is, in this embodiment, the at least one light-supplying component includes a bunch of optical fibers 110. In this embodiment, the handle 12 is furnished with an optical-fiber connector 126 which is connectable with another optical-fiber connector 262 located at one end of an optical-fiber cable 26. Another end of the optical-fiber cable 26 is also furnished with an optical-fiber connector 261 and is connected with an output connector 251 of a light source 25. The light source 25 complies with the safety regulations of electrical medical equipment and can provide light for medical purposes via the output connector 251. A bunch of optical fibers 110 are furnished inside the disposable integrated endoscope 10 and extending between the optical-fiber connector 126 and the chip carrier 112 adjacent to the front end opening of the outer tube 111. The light provided by the light source 25 is transmitted into the handle 12 of the disposable integrated endoscope 10 via the optical-fiber cable 26 and the optical-fiber connector 126, and then further transmitted to the front surface (carrying surface) of the chip carrier 112 via the optical fibers 110. As shown in FIG. 11, the front ends of these optical fibers 110 are arranged and distributed to surround on the outer periphery of the image sensors 113, such that, the light rays emitted out from these optical fibers 110 can provide an even and clear illumination effect for the external objects such as the internal tissues or organs of the human body.

While the present invention has been particularly shown and described with reference to a preferred embodiment, it will be understood by those skilled in the art that various changes in form and detail may be achieved without departing from the spirit and scope of the present invention.

What is claimed is:

1. A disposable integrated endoscope comprising:
an image capturing module for capturing images; said image capturing module further comprising:
  a hollow outer tube, extending a first length along a first direction and having a front end opening and a rear end opening;
  at least one image sensor, located in the outer tube and adjacent to the front end opening; said at least one image sensor being configured to capture images of an object outside the front end opening and generate image signals accordingly;
  at least one light-supplying component, located in the outer tube and adjacent to both the at least one image sensor and the front end opening; said at least one light-supplying component being configured to emit light to illuminate the object located outside the front end opening;
  a flexible circuit board, comprising an elongated strip and received inside the outer tube; a front end of the flexible circuit board being electrically connected to the at least one image sensor; a rear end of the flexible circuit board extending along the first direction and extending out of the rear end opening of the outer tube; and
  a heat-pipe, accommodated in the outer tube and extending along the first direction for a second length; a front end of the heat-pipe being located at a first location where the at least one image sensor and the at least one light-supplying component are also located, while a rear end of the heat-pipe being located at a second location where the rear end opening of the outer pipe is also located; said heat-pipe being configured to conduct a heat generated by the at least one image sensor toward the rear end opening of the outer pipe in order to provide a heat dissipation function;
a handle, connected to a rear portion of the outer tube of the image capturing module; said handle having an inner compartment;
an image-transmission circuit board, located within the inner compartment of the handle; the image-transmission circuit board being provided with a control unit which includes at least one integrated-circuit component capable of processing said image signals; the rear end of the flexible circuit board being electrically connected to the image-transmission circuit board; the image signals generated by the at least one image sensor being transmitted to the image-transmission circuit board via the flexible circuit board; the at least one integrated-circuit component included in the control unit being configured to convert the image signals into digital signals that are configured to be processed by a computer;

a cable module, connected to the handle; the cable module including a quick-coupling connector and a circuit board connector electrically connected to the quick-coupling connector; the quick-coupling connector being configured to connect with an external device; the circuit board connector being electrically connected to the image-transmission circuit board, so that the digital signals converted by the control unit are configured to be transmitted to the external device via the quick-coupling connector of the cable module, in addition, the external device is configured to provide power to the image-transmission circuit board via the cable module;

a chip carrier, located in the outer tube and adjacent to the front end opening; said chip carrier having a carrying surface perpendicular to the first direction and a rear surface opposite to the carrying surface; a circuit layout being provided on the chip carrier; the at least one image sensor being disposed on the carrying surface and electrically connected to the circuit layout of the chip carrier;

a front cover, covering the carrying surface of the chip carrier; said front cover being respectively provided with an opening at positions corresponding to the at least one image sensor and the at least one light-supplying component, such that a light-sensing surface of the at least one image sensor and a light-emitting surface of the at least one light-supplying component are respectively plugged into the corresponding openings and exposed to a front surface of the front cover; the front cover being plugged and fixed at the front end opening of the outer tube, such that the chip carrier together with the at least one image sensor and the at least one light-supplying component thereon are fixed to the front end opening of the outer tube by means of the front cover; the flexible circuit board being electrically connected to the circuit layout of the chip carrier;

a protective glass, covering the front surface of the front cover and corresponding to the light-sensing surface of the at least one image sensor;

a heat-pipe stand, capping on a front end of the heat-pipe; an outer diameter of the heat-pipe stand being corresponding to an inner diameter of the outer tube; the heat-pipe stand positioning and supporting the front end of the heat-pipe at a third location where the front end opening of the outer tube is also located; the heat-pipe stand having a front end surface; a thermal tape being provided on the front end surface of the heat-pipe stand; said thermal tape being attached and sandwiched between the front end surface of the heat-pipe stand and the rear surface of the chip carrier, such that a heat generated by the at least one image sensor is dissipated to the heat-pipe stand and the heat-pipe via the chip carrier and the thermal tape; and a first connector, furnished at the rear end of the flexible circuit board away from the chip carrier; the first connector being connected with a connector socket of the image-transmission circuit board.

2. The disposable integrated endoscope of claim 1, wherein the image capturing module further comprises a heat-shrinkable sleeve which covers outside of the heat-pipe, the heat-pipe stand and part of the flexible circuit board; by heating the heat-shrinkable sleeve, the heat-shrinkable sleeve is shrunk; such that the flexible circuit board attaches on an outer surface of the heat-pipe.

3. The disposable integrated endoscope of claim 1, wherein the at least one light-supplying component is light-emitting diode (LED); the at least one LED being disposed on the carrying surface and electrically connected to the circuit layout of the chip carrier; a heat generated by the at least one LED is dissipated to the heat-pipe stand and the heat-pipe via the chip carrier and the thermal tape; the number of the at least one LED is two, and these two LEDs are respectively located on upper and lower sides of the at least one image sensor.

4. The disposable integrated endoscope of claim 3, wherein the number of the at least one image sensor is two, and these two image sensors are adjacently arranged in a left and right side-by-side manner, and said two image sensors are both located between the two LEDs.

5. The disposable integrated endoscope of claim 1, wherein an indicator is arranged on an outer surface of the handle; the indicator indicates a position where a rotation angle of the at least one image sensor is 0 degrees.

6. The disposable integrated endoscope of claim 1, wherein the at least one image sensor is Complementary Metal Oxide Semiconductor (CMOS) image sensor; the image signals generated by the at least one image sensor are directly transmitted via the circuit layout on the chip carrier to the flexible circuit board and then further directly transmitted to the image-transmission circuit board; the control unit on the image-transmission circuit board provides functions that comply with the Mobile Industry Processor Interface (MIPI) specifications, which is configured to convert the image signals from the at least one image sensor into the digital signals that are configured to be processed by the computer.

7. The disposable integrated endoscope of claim 6, wherein the digital signals converted and generated by the control unit of the image-transmission circuit board comply with one of the following specifications: high-definition multimedia interface (HDMI) specification, DisplayPort (DP) specification, video graphics interface (VGA) specification, Digital Visual Interface (DVI) specification, or Universal Serial Bus (USB) specification.

8. The disposable integrated endoscope of claim 1, wherein the quick-coupling connector of the disposable integrated endoscope is connected with the external device; the external device is a rear-end device; the rear-end device is further connected to a medical industrial personal computer (IPC) via a universal serial port (USB) plug.

9. The disposable integrated endoscope of claim 1, wherein the quick-coupling connector of the disposable integrated endoscope is connected with the external device; the external device is an industrial personal computer (IPC).

10. The disposable integrated endoscope of claim 1, wherein the at least one light-supplying component includes a plurality of optical fibers; said optical fibers are furnished inside the disposable integrated endoscope and extending between an optical-fiber connector furnished on the handle and the chip carrier; front ends of the optical fibers are arranged and distributed to surround on an outer periphery of the at least one image sensor.

11. The disposable integrated endoscope of claim 9, wherein the at least one integrated-circuit component includes a Field Programmable Gate Array (FPGA) which is a semiconductor integrated circuit where electrical functionality is customized to accelerate processing of said image signals; additionally, an image signal processing (ISP) IC is furnished inside the IPC for accepting and further processing the image signals processed by the FPGA.

* * * * *